United States Patent [19]
Rambach

[11] Patent Number: 5,846,761
[45] Date of Patent: Dec. 8, 1998

[54] **CULTURE MEDIUM FOR THE DETECTION OF *E. COLI* AND PROCESS FOR ITS USE**

[76] Inventor: Alain Rambach, 73 boulevard du Montparnasse, 75006 Paris, France

[21] Appl. No.: 701,553

[22] Filed: Aug. 22, 1996

Related U.S. Application Data

[63] Continuation of Ser. No. 411,609, Apr. 7, 1995, abandoned.

[30] Foreign Application Priority Data

Oct. 7, 1992 [FR] France ................................. 94 11879

[51] Int. Cl.$^6$ .............................. C12Q 1/04; C12Q 1/02; C12Q 1/54; C12N 1/00
[52] U.S. Cl. ............................... 435/34; 435/29; 435/14; 435/849; 435/4
[58] Field of Search .................................. 435/34, 29, 4, 435/849, 14

[56] References Cited

U.S. PATENT DOCUMENTS

| 4,923,804 | 5/1990 | Ley et al. .................................. 435/34 |
| 5,210,022 | 5/1993 | Roth et al. ................................. 435/34 |

FOREIGN PATENT DOCUMENTS 94080043   4/1994   WIPO .

OTHER PUBLICATIONS

Ogden et al, "Letters in Applied Microb," vol. 13, pp. 212–215, 1991. Month not available.

Jefferson et al, Pro Natl Acad. Sci., vol. 83, pp. 8447–8451, Nov. 1986.

Letters in Applied Microbiology, vol. 13, No. 4, Oct. 1, 1991, Blackpool UK, pp. 212–215.

Zentralblatt fur Hygiene und Umweltmedizin, vol. 189, No. 3, 1989, Stuttgart Brd, pp. 225–234 month not available.

*Primary Examiner*—Louise N. Leary
*Attorney, Agent, or Firm*—Blakely Sokoloff Taylor & Zafman

[57] ABSTRACT

A culture medium for the detection of *E. coli* and a process for the detection of *E. coli* utilizing the culture medium are disclosed. The culture medium includes a known culture medium for *E. coli*, a chromogenic compound derived from indolyl-glucuronic acid derivatives or salts thereof and a non-chromogenic alkyl, alkenyl, or aryl glucuronic acid derivative or salt thereof. The indolyl-glucuronic acid derivative or salts thereof serve as substrates for the beta-D-glucuronidase (GUS) enzyme that by cleavage of the substrate, gives a colored or flourescent derivative. The indolyl-glucuronic acid derivative in the culture medium is between 1:1 and 1:19, and is preferably 1:1 to 1:3. The culture medium may further contain a phosphate at a concentration greater than one gram per liter, and preferably between four and ten grams per liter. The process relates to inoculating the culture medium with a sample or an inoculum obtained from the sample and monitoring the medium for the presence of *E. coli*.

23 Claims, No Drawings

CULTURE MEDIUM FOR THE DETECTION OF E. COLI AND PROCESS FOR ITS USE

This is a continuation of application Ser. No. 08/411,609 filed Apr. 7, 1995 now abandoned.

The present invention relates to a new culture medium intended especially for the detection of Escherichia coli.

There are currently a number of culture media for the detection of Escherichia coli which is one of the microorganisms whose detection is the most frequent.

The detection of E. coli is very important especially in the food industries, for the control of water, but also in medicine, knowing that in this medium, E. coli may be a pathogenic agent but also an agent revealing certain types of contamination. Given the diversity of the applications and of the conditions in which the detection has to be carried out, it is therefore necessary to be able to have a detection medium which is simple and rapid to use but which is also reliable.

Now, the trials which have been carried out show that most of the culture media currently used, while they allow the detection of a large number of Escherichia coli strains, do not nevertheless allow the detection, in a simple manner, of 100% of the contaminations. Now, it is known that generally a probability of the order of 90% cannot be considered as satisfactory because in most cases, this type of probability is completely unacceptable for obvious reasons. The pathogenic microorganisms which may be present in these non-counterselected samples will tend to spread because they cannot be detected by traditional methods.

Accordingly, the present invention constitutes a significant advance insofar as it proposes culture media allowing the detection, in a simple manner, of a much larger number of E. coli contaminations compared with existing media.

More particularly, this is a culture medium intended for the detection of E. coli, characterized in that it contains, in addition to a culture medium for E. coli, as chromogenic agent, a combination of:

a chromogenic compound derived from indolylglucuronic acid or from its salts, which are substrates for the GUS enzyme and an alkyl, alkenyl or arylglucuronic acid derivative or salt.

Culture media for the detection of Escherichia coli are known and will not be described again in detail below, but will be mentioned only in the examples.

As regards the chromogenic compounds, they are chromogenic agents of which some are already used in the detection of E. coli and which involve indolylglucuronic acid derivatives. These chromogenic compounds are substrates for the beta-D-glucuronidase or GUS enzyme which, by cleavage of the substrate, gives a colored and/or fluorescent derivative for example.

Among these indolylglucuronic acid derivatives, there should be mentioned more particularly the derivatives of halo-3-indolylglucuronic acids and their corresponding salts and still more particularly the compounds chosen from 5-bromo-4-chloro-3-indolyl-beta-D-glucuronic acid, the sodium and cyclohexylammonium salts, 5-bromo-6-chloro-3-indolyl-beta-D-glucuronic acid, the sodium and cyclohexylammonium salts, 6-chloro-3-indolyl-beta-D-glucuronic acid, 5-bromo-3-indolyl-beta-D-glucuronic acid, 3-indoly-beta-D-glucuronic acid, their sodium and cyclohexylammonium salts.

These compounds are used according to the present invention in combination with derivatives of alkylated, alkenylated and/or arylated glucuronic acid. They may be $C_1$ to $C_3$ alkylated or alkenylated, especially methylated, derivatives or arylated derivatives of the phenyl or substituted phenyl type as well as the corresponding salts. Among the most effective compounds according to the present invention, there should be mentioned most particularly phenylglucuronic acid as well as its salts (especially its alkali and alkaline-earth metal salts and its ammonium-derived salts such as for example the salts of the cyclohexylammonium type).

According to the nature of the chromogenic agent used, the colors which will reveal the presence of E. coli will vary, one of the advantages of this process is that it makes it possible, with relatively low chromogen concentrations, to obtain detections of the E. coli contaminations of close to 100%.

Preferably, the chromogenic compound/glucuronic acid derivative weight ratio is between 1/1 and 1/10, preferably between 1/1 and 1/3.

For example, it will be possible to use concentrations of chromogenic compounds of less than or equal to 50 mg/l and optionally of the order of 30 mg/l, with quantities of glucuronic acid derivatives of close to 100 mg/l.

The medium according to the invention may, in addition, be advantageously supplemented with phosphate, preferably at a concentration greater than 1 g/l, more particularly between 4 g/l and 10 g/l.

The present invention also relates to a process for the detection of E. coli strains in any sample, characterized in that the culture medium as described above is inoculated with the said sample and/or an inoculum obtained from the said sample and in that the color or the fluorescence characteristic of the presence of E. coli is detected.

This culture medium according to the invention also has, compared with the prior art media, the advantage of being capable of being used according to any of the methods known in this type of technology. In particular, it is possible, with the media according to the invention, to envisage inoculation in the bulk of the medium.

This aspect of the invention is all the more unexpected as, since the chromogens derived from indolyl do not function under anaerobic conditions, it could have been thought that the process of inoculation in the bulk is incompatible with their use in the medium according to the invention.

Finally, it is experimentally observed that by virtue of the culture medium according to the present invention, the appearance of true positives is accelerated, false negatives are eliminated and practically 100% of the E. coli contaminations are detected.

The examples below are intended to demonstrate other characteristics and advantages of the present invention.

EXAMPLE 1

Detection of E. coli strains

Various E. coli strains are isolated on M medium (in g/l: meat extract 1; yeast extract 2; peptone 5; sodium chloride 5; agar 15; sodium deoxycholate 1.5; 5-bromo-4-chloro-3-indolylglucuronide 0.05).

The dishes are incubated at 37° C. and the blue color of the colonies is observed after incubating for 24 hours.

One of the three strains, E. coli 297-3, is only detected after addition of phenyl glucuronide (Table 1).

TABLE 1

| E. coli Strain | color M medium | color M medium 100 mg/l Phenyl glucuronide |
|---|---|---|
| 289-3 | + | + |
| 297-3 | − | + |
| 366-1 | + | + |

The addition of phosphate also makes it possible to enhance the sensitivity of the medium according to the invention (Table 2).

TABLE 2

| | color of the E. coli colonies | |
|---|---|---|
| | incubation 18 h | incubation 24 h |
| M medium | − | +/− |
| M medium phenyl glucuronide 100 mg/l phosphate 8 g/l | ++ | ++ |

EXAMPLE 2

Comparison with the PTX medium

The PTX medium comprises, as chromogenic agent, 5-bromo-4-chloro-3-indolyl-beta-D-glucuronic acid. It is a medium having the same base as the medium PTG which is recognized in France to be useful in relation to an E. coli detection medium (Baylac et al, médecine et armees, 1990, 18, p.305–308).

The PTX medium (in g/l: yeast extract 3; peptone 5; phosphate 0.3; tergitol 0.1; agar 15; chromogenic compound 0.05) was compared with a medium according to the invention, PTX supplemented with phenyl glucuronide (0.1 g/l) and with phosphate (8 g/l).

TABLE 3

| | color of the E. coli colonies | |
|---|---|---|
| | incubation 18 h | incubation 24 h |
| PTX medium | − | +/− |
| PTX medium phenyl glucuronide 100 mg/l phosphate 8 g/l | ++ | ++ |

EXAMPLE 3

Analysis of Minced Steak Samples

Steak samples are examined by the standard method of grinding dilution and plating.

The agar according to the invention is compared with a commercial device on a film where the E. coli cells are also detected by a simple specific color.

The results indicate that the proportion of E. coli colonies detected according to the invention is higher than the technique using a film giving a specific color to the E. coli colonies.

TABLE 4

| Minced steak samples | E. coli colonies detected on agar according to the invention | E. coli colonies detected on a commercial film for E. coli |
|---|---|---|
| 362 | 0 | 0 |
| 365 | 0 | 0 |
| 371 | 120 | 50 |
| 368 | 102 | 50 |
| 367 | 0 | 56 |
| 363 | 2 | 0 |
| 370 | 40 | 11 |
| 379 | 0 | 0 |
| 380 | 200 | 29 |
| 382 | 3 | 1 |
| 383 | 9 | 4 |
| 384 | 1 | 3 |
| 386 | 3 | 2 |
| 3006 | 0 | 0 |
| 3007 | 0 | 0 |
| 3008 | 192 | 83 |

I claim:

1. A culture medium for the detection of E. coli, comprising, in addition to a culture medium for E. coli, as chromogenic agents, a combination of:
    a chromogenic compound derived from indolyl-glucuronic acid which is a substrate for the beta-D-glucuronidase (GUS) enzyme; and
    an alkyl, alkenyl or aryl glucuronic acid derivative.

2. The culture medium according to claim 1, wherein the chromogenic compound is chosen from halo-3-indolyl-glucuronic acids and the corresponding salts.

3. The culture medium according to claim 2, wherein the chromogenic compound is selected from the group consisting of 5-bromo-4chloro-3-indolyl-beta-D-glucuronic acid and the sodium and cyclohexylammonium salts, 5-bromo-6-chloro-3-indolyl-beta-D-glucuronic acid and the sodium and cyclohexylammonium salts thereof, 6-chloro-3-indolyl-beta-D-glucuronic acid and the sodium and cyclohexylammonium salts thereof, 5-bromo-3-indolyl-beta-D-glucuronic acid and the sodium and cyclohexylammonium salts thereof, and indolyl-beta-D-glucuronic acid and the sodium and cyclohexylammonium salts thereof.

4. The culture medium according to one of claims 1, 2, or 3, wherein the chromogenic compound/glucuronic acid derivative weight ratio is between 1/1 and 1/10.

5. The culture medium according to claim 4 further comprising 50 mg/l of the chromogenic compound for about 100 mg/l of glucuronic acid derivative.

6. The culture medium according to claim 1 further comprising phosphate at a concentration greater than 1 g/l.

7. A process for the detection of E. coli in a sample, comprising:
    providing a culture medium comprising, in addition to a culture medium for E. coli, a chromogenic compound derived from indolyl-glucuronic acid, and an alkyl, alkenyl or aryl glucuronic acid derivative;
    inoculating with the sample or an inoculum obtained from said sample; and
    monitoring said medium for the presence of E. coli.

8. The process for the detection of E. coli according to claim 7, characterized in that the inoculation is carried out in the bulk of the culture medium.

9. The culture medium of claim 4, wherein said chromogenic compound/glucuronic acid derivative weight ratio is between 1/1 and 1/3.

10. The culture medium of claim 6, wherein said phosphate concentration of said culture medium is between 4 g/l and 10 g/l.

11. The process of claim 7, wherein said chromogenic compound of said culture medium is halo-3-indolylglucuronic acid or its salts.

12. The process of claim 11, wherein said chromogenic compound is selected from the group consisting of 5-bromo-4-chloro-3-indolyl-beta-D-glucuronic acid and the sodium and cyclohexylammonium salts thereof, 5-bromo-6-chloro-3-indolyl-beta-D-glucuronic acid and the sodium and cyclohexylammonium salts thereof, 6-chloro-3-indolyl-beta-D-glucuronic acid and the sodium and cyclohexylammonium salts thereof, 5-bromo-3-indolyl-beta-D-glucuronic acid and the sodium and cyclohexylammonium salts thereof, and indolyl-beta-D-glucuronic acid and the sodium and cyclohexylammonium salts thereof.

13. The process of claim 7, wherein said chromogenic compounds/glucuronic acid derivative weight ratio is between 1/1 and 1/10.

14. The process of claim 13, wherein said chromogenic compound/glucuronic acid derivative weight ratio is between 1/1 and 1/10.

15. The process of claim 13, wherein said culture medium further comprises 50 mg/l of said chromogenic compound for about 100 mg/l of glucuronic acid derivative.

16. The process of claim 7, wherein said culture medium further comprises phosphate at a concentration greater than 1 g/l.

17. The process of claim 16, wherein said phosphate concentration in said culture medium is 4 g/l and 10 g/l.

18. A culture medium for the detection of *E. coli*, consisting of, in addition to a culture medium for *E. coli*, as chromogenic agents, a combination of:

a chromogenic compound derived from indolyl-glucuronic acid which is a substrate for the beta-D-glucuronidase enzyme;

phenyl-glucuronide; and phosphate.

19. The culture medium according to claim 18, wherein the chromogenic compound/phenyl-glucuronide weight ratio is between 1/1 and 1/10.

20. The culture medium of claim 18, wherein the phosphate concentration of said culture medium is between 4 g/l and 10 g/l.

21. A culture medium for the detection of *E. coli*, comprising, in addition to a culture medium for *E. coli*, a combination of:

a chromogenic compound derived from indolyl-glucuronic acid which is a substrate for the beta-D-glucuronidase (GUS) enzyme; and a non-chromogenic alkyl, alkenyl or aryl glucuronic acid derivative.

22. The culture medium of claim 21, wherein the chromogenic compound/glucuronic acid derivative weight ratio is between 1/1 and 1/10.

23. The culture medium of claim 22 comprising 50 mg/l of the chromogenic compound for about 100 mg/l of the glucuronic acid derivative.

* * * * *

UNITED STATES PATENT AND TRADEMARK OFFICE
CERTIFICATE OF CORRECTION

PATENT NO. : 5,846,761

DATED : December 8, 1998

INVENTOR(S) : Rambach

It is certified that error appears in the above-identified patent and that said Letters Patent is hereby corrected as shown below:

In column 4, line 35, delete "5-bromo-4chloro-3-indolyl-beta-D-glucuronic" and insert -- 5-bromo-4-chloro-3-indolyl-beta-D-glucuronic --.

In column 4, line 44, delete "claims" and insert -- claim --.

Signed and Sealed this

Twenty-fourth Day of April, 2001

*Attest:*

NICHOLAS P. GODICI

*Attesting Officer*   Acting Director of the United States Patent and Trademark Office